United States Patent [19]
Brown

[11] Patent Number: 5,496,337
[45] Date of Patent: Mar. 5, 1996

[54] DEVICE FOR GAUGING SUTURE DEPTH

[76] Inventor: Randall L. Brown, 4637 Chelsea Dr., Baton Rouge, La. 70809

[21] Appl. No.: 417,795

[22] Filed: Apr. 6, 1995

[51] Int. Cl.$^6$ ............................ A61B 17/04; A41D 13/08
[52] U.S. Cl. ................. 606/148; 606/1; 2/161.7; 2/163
[58] Field of Search .................. 606/1, 148, 144; 2/160, 163, 167.7

[56] References Cited

U.S. PATENT DOCUMENTS 3,511,242  5/1970  Agnone .................... 606/148
4,985,038  1/1991  Lyell ........................ 606/148
5,140,709  8/1992  Cohn et al. ................. 2/163

*Primary Examiner*—Gary Jackson
*Attorney, Agent, or Firm*—Roy, Kiesel & Tucker

[57] ABSTRACT

A device for gauging the depth of suture penetration is provided. The device has a sheath with a closed end, where the interior of the sheath is sized to fit over a finger, and a plurality of tines positioned on the closed end so that a suturing device has at least one path across the surface of the closed end unobstructed by the tines. The sheath is generally constructed of material resistant to puncture or penetration by a suturing device. The device can be incorporated into a fingermember of a glove.

18 Claims, 3 Drawing Sheets

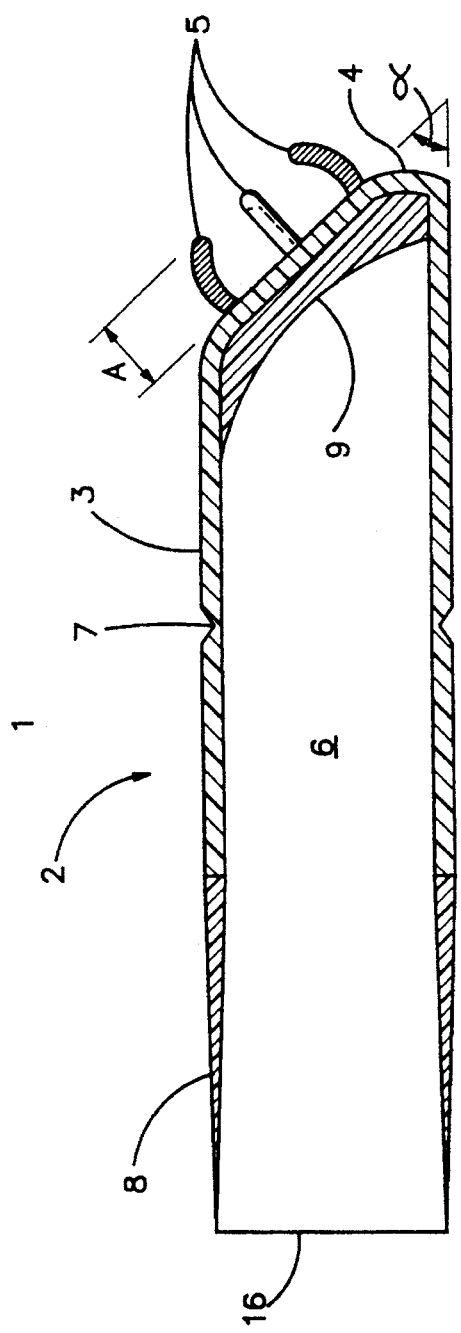
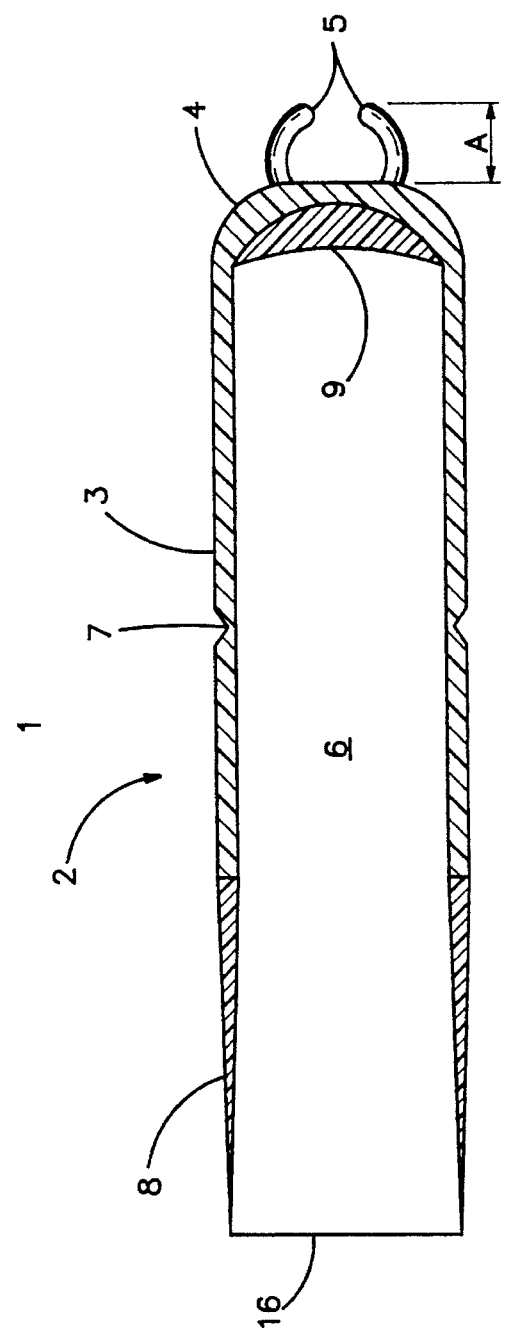

DEVICE FOR GAUGING SUTURE DEPTH

BACKGROUND OF THE INVENTION

1. Field of the Invention

This invention relates, generally, to devices for placement of sutures in tissues, and more particularly, devices to gauge the depth of penetration of sutures in tissue.

2. Prior Art

In surgery, it is sometimes necessary to attach or suture materials to a first tissue, such materials including: an implanted device, an artificial tissue, a second tissue, or even the first tissue if that first tissue has become torn or separated. The suturing method requires that a suturing device, usually a needle with attached suturing material, first be passed through the material to be attached, and then second, passed into the attachment tissue, thereby joining material and tissue by sutures. The order of the above steps can be reversed.

The required depth of penetration of the suture into the tissue can vary depending upon the materials to be attached, the type of attachment tissue, the thickness of the suturing device and the strength of the attachment desired. The prior methods for gauging the depth of suture penetration depended upon the "look and feel" of the tissues and suture device. That is, in placing the suture, the doctor would position a finger under the attachment tissue and would feel for the needle as it passed into the attachment tissue, the penetration depth being determined by the doctor's subjective estimate based upon the feel of the penetration and by visual inspection, where possible. Because the "look and feel" method is subjective, proper suture depth penetration cannot be consistently or accurately obtained. Further, with the increased concern over communicable blood-borne diseases, the "look and feel" method presents a danger because the suturing device, if depth of penetration is misjudged, can penetrate the doctor's finger causing the doctor's blood to mix with that of the tissue. Thus, caution on the doctor's part is required; however, that caution must be balanced against the need to attain a suture with the desired penetration into the attachment tissue.

SUMMARY OF THE INVENTION

Therefore, it is an object of the present invention to provide an apparatus which provides a reliable and reproducible gauge for objective depth selection during suture placement.

Another object of the present invention is to provide an apparatus for placement over a finger which creates a barrier resistant to penetration by a suturing device.

These and other objects, advantages, and features of this invention will be apparent from the following descriptions of the invention.

Accordingly, a device for placement over a finger having at least one finger joint is provided comprising an elongated sidewall structured to bend at the finger joint of an inserted finger, a closed end, and tines placed on the closed end and projecting outwardly therefrom. The tine length determines the depth of penetration of the suture. The sidewall and closed end may be constructed of materials resistant to penetration by a suturing device. The closed end may form an angle other than 90 degrees with the sidewalls.

BRIEF DESCRIPTION OF THE DRAWINGS

FIG. 3 is a lengthwise cross sectional view of the embodiment depicted in FIG. 1.

FIG. 4 is a lengthwise cross sectional view of the embodiment depicted in FIG. 2.

DETAILED DESCRIPTION

Figure 1:
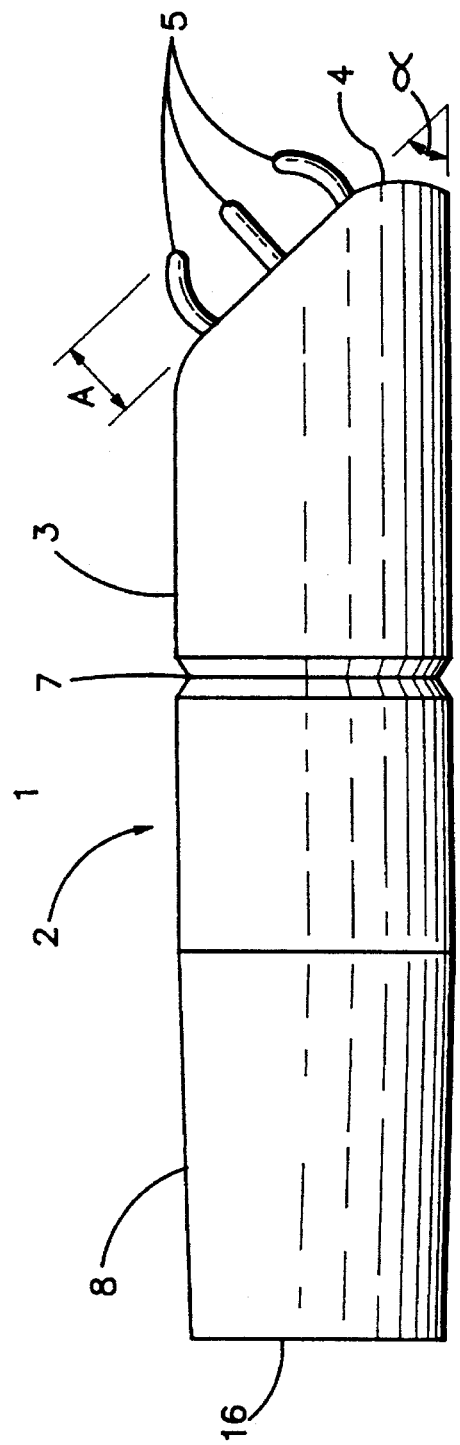
FIG. 1 is a perspective view of an embodiment of the invention.
Figure 2:
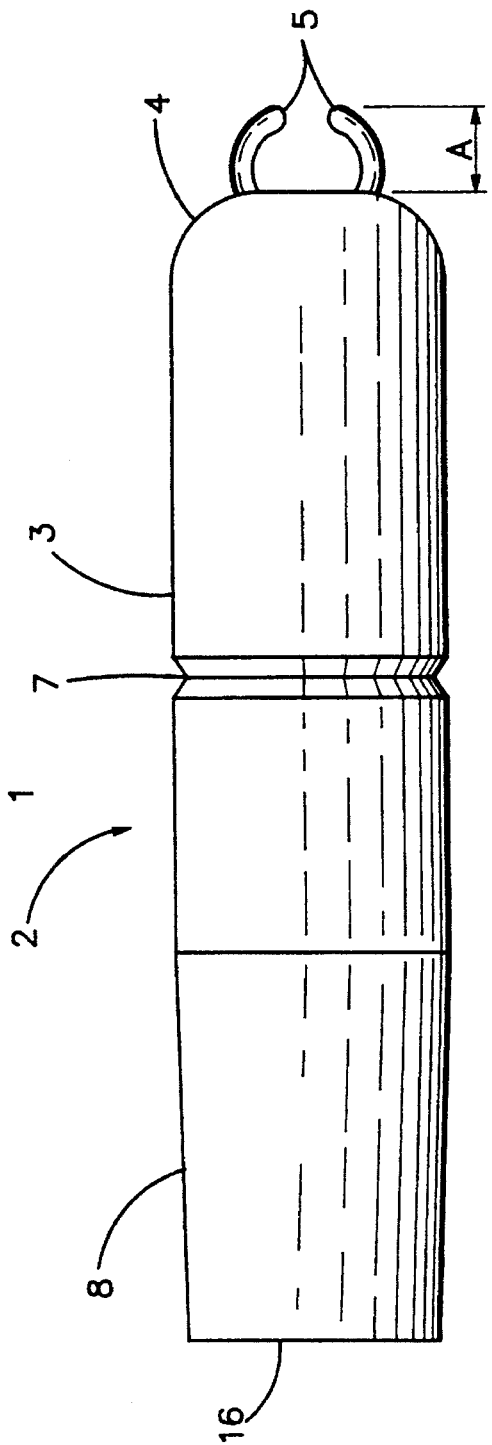
FIG. 2 is a perspective view of a second embodiment of the invention.

As shown generally in FIGS. 1 through 4, the device for gauging suture penetration 1 generally comprised a sheath 2 forming an elongated sidewall 3 and a closed end 4. A plurality of tines 5 is positioned on the closed end 4. The sidewall 3 terminates in an opening 16 opposite the closed end 4. The sidewall 3, the closed end 4, and the opening 16 define an interior 6. The opening 16 and the interior 6 are sized to permit a least one finger joint of a human finger (not shown) to be inserted into the interior 6. The interior 6 can be of varying sizes to accommodate different finger sizes. The sheath 2 may form one fingermember of a surgical glove (not shown).

A resilient layer 9 of material may be disposed on the interior side of the closed end 4 to provide cushioning to the fingertip of the finger inserted in the interior 6. The resilient layer 9 further provides a medium through which a feeling of pressure, exerted by a suturing device on the closed end, may be communicated to the fingertip of the finger inserted into the interior 6. Such a pressure feeling provides feedback to the person wearing the device concerning the degree of penetration of the suturing device through the tissue.

A finger joint area 7 is preferably incorporated into the sidewall 3 adjacent to a finger joint (not shown) of a finger inserted into the interior 6 which allows the finger to flex when inserted in the interior 6. The finger joint area 7 is constructed of a flexible material, such as latex or other flexible plastic, which can be either stretched or compressed without splitting or rupturing. Multiple finger joint areas 7 can be incorporated if the interior 6 is sized to accommodate more than one finger joint.

During surgery, body fluids can migrate into the interior 6, tending to cause the sheath 2 to slip off the inserted finger joint. A finger gripping section 8 constructed of elastic material is preferably incorporated into the elongated sidewall 3 adjacent to the opening 16 to frictionally grip the finger joint, reducing the likelihood of the sheath 2 slipping off the finger joint. If the sheath 2 forms one fingermember of a surgical glove, the remaining glove acts as a finger gripping section 8.

The sheath 2 may be composed, in part, of hardened plastic or lightweight metals to lessen the likelihood of a suturing device (not shown), such as a needle, from penetrating the sheath 2. Any material resistant to needle penetration and suitable for exposure to human tissue could be used for sheath 2 construction. Because the closed end 4 of the sheath 2 is more likely to be exposed to the suturing device, it is preferable that at least the closed end 4 be constructed of hardened plastic or the like. The sheath 2 may also be of multiple layer construction, where at least one layer is constructed of a material substantially resistant to penetration by a suturing device.

As shown in FIGS. 1 and 3, the closed end 4 may form an angle α other than 90 degrees with the sidewall 3. The angle α desired in a particular embodiment of the device will be dependent upon the surgical procedure under consideration. For retro-pubic surgical procedures, an angle α of 30 or 90 degrees has been found suitable. The angle α chosen will depend, in part, on the angle formed between the finger joint and the tissue to be sutured.

Positioned on the closed end 4 are a plurality of tines 5 projecting outwardly from the closed end 4. Preferably, the distance B separating adjacent tines 5 is, at a minimum, sufficient to allow a suturing device to pass unobstructed between adjacent tines. The tines 5, when pressed against a tissue (not shown) supports and elevates the tissue in the immediate area of the closed end 4. The height of the elevated tissue above the closed end 4 will depend upon the length A of the tines 5. The desired elevation height will depend on the desired depth of penetration of the suture into the tissue. Where it is desired for the suture to completely penetrate the tissue, a longer tine length A is preferable, with the tine length A dependent, in part, on the type of suturing device, including the thickness and curvature of the suturing device. For complete penetration of most tissue types, a tine length A of 6 mm to 10 mm has been found preferable. When only partial penetration of the suture into the tissue is required, a length in the range of 1 mm to 5 mm has been found preferable.

Figure 6:
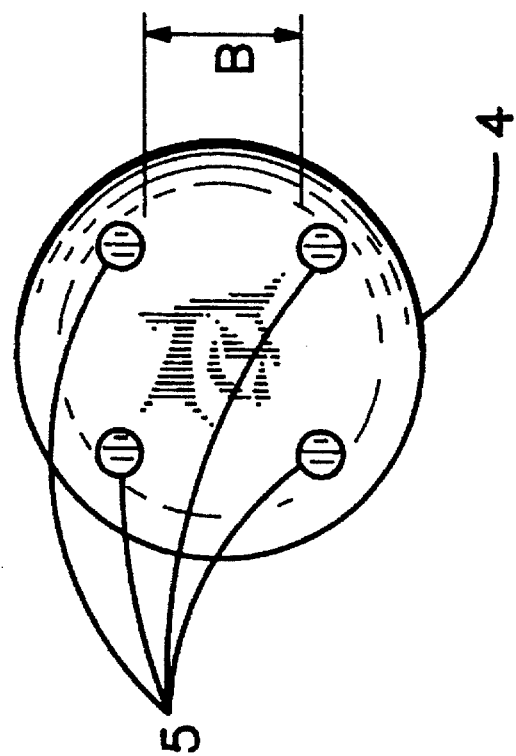
FIG. 6 is an end view of the closed end of a second embodiment of the invention.
Figure 5:
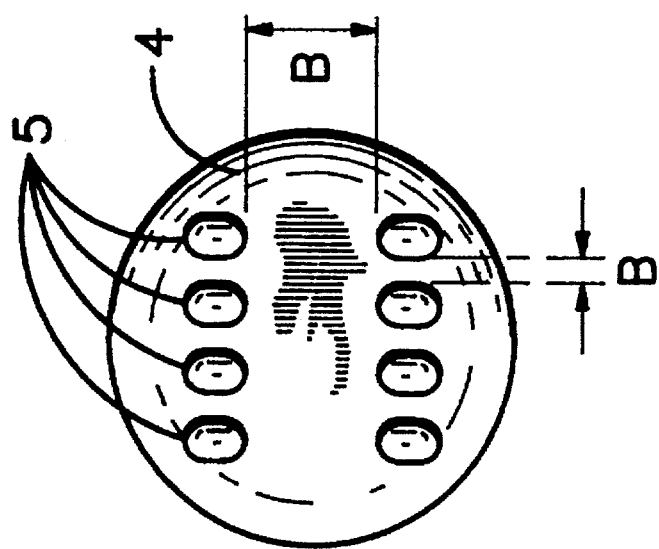
FIG. 5 is an end view of the closed end of one embodiment of the invention.

As is shown in FIG. 5, the tines 5 may be placed in two opposing rows on the closed end 4. Alternatively, as is shown in FIG. 6, the tines 5 may be placed equidistant around the perimeter area of the closed end 4. In any placement of the tines 5 on the closed end 4, it is important that at least one path across the closed end 4 through the tines 5 be available for a suturing device to pass unobstructed. For instance, if the tines 5 are equally spaced around the perimeter of the closed end 4, it has been found that an even number of tines 5 is preferred; in this instance, the space between two adjacent tines 5 will be directly opposite another space, providing a clear path for a suturing device across the closed end 4.

As is shown in FIGS. 1 through 4, the tines 5 may also be arcuate. Arcuate shape tines 5 are less likely to catch and potentially tear tissue, either in use of the device, or in placement or withdrawal of the device.

Finally, the entire device can be incorporated into one fingermember of a surgical glove.

There are, of course, many other alternative embodiments and modifications which are intended to be included within the scope of the following claims.

What I claim is:

1. An apparatus to determine the depth to which sutures are placed in tissues, which comprises:
   (a) a sheath forming an elongated sidewall and a closed end defining an opening opposite said closed end leading into an interior space, said opening and interior space sized to permit at least a portion of a finger having at least one finger joint to be inserted through said opening and into said interior space; and
   (b) a plurality of separated tines affixed to and projecting outwardly from said closed end.

2. An apparatus according to claim 1 wherein said elongated sidewall includes at its perimeter area forming said opening a finger gripping section constructed of elastic material which frictionally grips said finger to retard the removal of said finger from said interior space.

3. An apparatus according to claim 1 wherein said closed end is angularly joined to said elongated sidewall.

4. An apparatus according to claim 3 wherein said closed end is joined at an angle of 30 degrees to said elongated sidewall.

5. An apparatus according to claim 1 wherein said elongated sidewall comprises a finger joint area constructed of flexible material and adapted to be positioned opposite said one of said finger joints of said finger.

6. An apparatus according to claim 1 wherein said closed end is constructed from a material substantially resistant to suture device puncture.

7. An apparatus according to claim 6 wherein at least that portion of said elongated sidewall adjacent to said closed end is constructed from a material substantially resistant to suture device puncture.

8. An apparatus according to claim 6 wherein said closed end is constructed of at least two layers of material, one of said layers constructed from said material substantially resistant to suture needle puncture.

9. An apparatus according to claim 1 wherein said tines are positioned to form at least one path across said closed end, said path being sized to permit a suturing device to pass across said closed end unobstructed by said tines.

10. An apparatus according to claim 9 wherein said tines are 1 mm to 10 mm in length.

11. An apparatus according to claim 9 wherein said tines are arcuate in shape.

12. An apparatus according to claim 9 wherein there are an even number of tines.

13. An apparatus according to claim 9 wherein said tines are affixed to the area of said closed end adjacent to said elongated sidewall.

14. An apparatus according to claim 13 wherein said tines are equally spaced from one another.

15. An apparatus according to claim 1 wherein a layer of resilient material is disposed on the interior side of said closed end.

16. An apparatus according to claim 5 wherein said sheath forms one fingermember of a glove.

17. On a surgical glove having fingermembers, each fingermember having a closed end, an apparatus to determine the depth to which sutures are placed in tissues which comprises a plurality of separated tines affixed to and projecting outwardly from at least one of said closed ends of said fingermembers.

18. An apparatus according to claim 17 wherein said tines are positioned to form at least one path across said closed end, said path being sized to permit a suturing device to pass across said end of said fingermember unobstructed by said tines.

* * * * *

UNITED STATES PATENT AND TRADEMARK OFFICE
CERTIFICATE OF CORRECTION

PATENT NO. : 5,496,337

DATED : March 5, 1996

INVENTOR(S) : Randall L. Brown

Page 1 of 2

Figure 7:
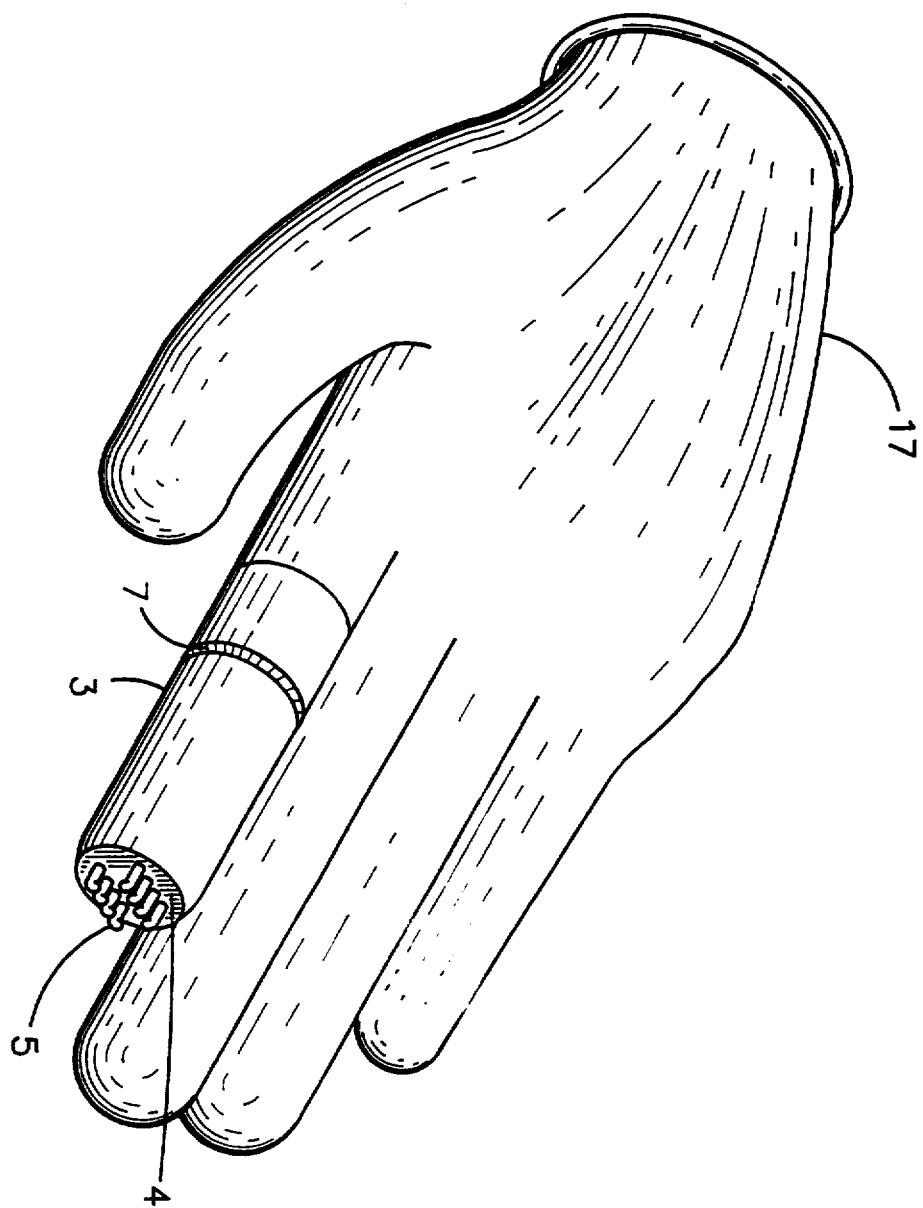

It is certified that error appears in the above-identified patent and that said Letters Patent is hereby corrected as shown below:

In the drawings, add Figure 7.

Column 2, insert a new line after Line 10 reading:
"Figure 7 is a prospective view of the invention as embodied in a glove."

Column 3, Line 44, after "glove" insert -as shown in Figure 7-.

Signed and Sealed this

Second Day of July, 1996

Attest:

Attesting Officer

BRUCE LEHMAN

Commissioner of Patents and Trademarks